United States Patent [19]

Lewis et al.

[11] Patent Number: 4,804,799

[45] Date of Patent: Feb. 14, 1989

[54] DEHYDROGENATION CATALYST

[75] Inventors: Gregg E. Lewis; Allen R. Smith; Fred A. Sherrod, all of Lake Jackson, Tex.

[73] Assignee: The Dow Chemical Company, Midland, Mich.

[21] Appl. No.: 90,807

[22] Filed: Aug. 28, 1987

[51] Int. Cl.$^4$ .......................... C07C 5/327; B01J 23/02
[52] U.S. Cl. .................................. 585/444; 585/443; 585/445; 502/304
[58] Field of Search ...................... 585/443, 444, 445; 502/304

[56] References Cited

U.S. PATENT DOCUMENTS

| | | | |
|---|---|---|---|
| 1,985,844 | 12/1934 | Suida | 585/26 |
| 2,036,410 | 4/1936 | Graves | 585/403 |
| 2,370,797 | 3/1945 | Kearby | 585/444 |
| 2,370,798 | 3/1945 | Kearby | 585/444 |
| 2,395,875 | 3/1946 | Kearby | 585/444 |
| 2,408,140 | 9/1946 | Gutzeit | 585/631 |
| 2,414,585 | 1/1947 | Eggertsen et al. | 585/444 |
| 2,418,888 | 4/1947 | Kearby | 502/329 |
| 2,418,889 | 4/1947 | Kearby | 502/328 |
| 2,426,829 | 9/1947 | Kearby | 585/445 |
| 2,866,790 | 12/1958 | Pitzer | 585/444 |
| 3,223,743 | 12/1965 | MacFarlane | 585/441 |
| 3,360,579 | 12/1967 | Hills et al. | 585/445 |
| 3,386,053 | 6/1968 | Lee | 332/31 T |
| 3,448,058 | 6/1969 | Arnold | 502/174 |
| 3,542,897 | 11/1970 | Wattlmenn | 585/663 |
| 3,904,552 | 9/1975 | O'Hara | 502/304 |
| 4,064,187 | 12/1977 | Soderquist et al. | 585/444 |
| 4,098,723 | 7/1978 | Riesser | 585/531 |
| 4,134,858 | 1/1979 | Courty | 585/445 |
| 4,144,197 | 3/1979 | Riesser | 585/445 |
| 4,460,706 | 7/1984 | Imanari et al. | 585/444 |
| 4,467,046 | 8/1984 | Smith et al. | 585/445 |
| 4,492,770 | 7/1985 | Blanchard et al. | 502/304 |
| 4,565,899 | 1/1986 | Burress | 585/444 |

FOREIGN PATENT DOCUMENTS

| | | | |
|---|---|---|---|
| 487670 | 10/1952 | Canada | 585/445 |
| 0206193 | 12/1986 | European Pat. Off. | 502/304 |
| 3442636 | 5/1986 | Fed. Rep. of Germany | 502/304 |

*Primary Examiner*—Asok Pal
*Attorney, Agent, or Firm*—A. Cooper Ancona

[57] ABSTRACT

A dehydrogenation catalyst containing iron and promoted with potassium and cerium has been shown to have improved activity when a copper compound is added thereto as a component. The improvement in activity is obtained without substantially sacrificing selectivity.

42 Claims, No Drawings

DEHYDROGENATION CATALYST

BACKGROUND OF THE INVENTION

This invention relates to improved catalysts for the dehydrogenation of hydrocarbons to corresponding more-unsaturated hydrocarbons, more particularly, to the production of vinyl aromatic hydrocarbons from alkyl aromatic hydrocarbons and to the production of olefins from the corresponding more-saturated aliphatic hydrocarbons.

The vinyl benzenes and butadienes play a particularly important role in the preparation of synthetic rubbers, plastics and resins. The polymerization of styrene, for example, with various comonomers such as butadiene to produce synthetic rubbers is well known as is the polymerization of styrene to produce polystyrene resins.

Styrene and butadiene are typically produced from ethylbenzene and butylene, respectively, by dehydrogenation over solid catalysts in the presence of steam and at temperatures ranging from 500° to 800° C. The class of catalysts found to be the most effective for this process contains a predominant amount of iron oxide, promoted by potassium carbonate, and stabilized by chromium oxide.

The activity of a catalyst is measured by the amount of starting material converted at a given temperature to another material and the selectivity is the percent of the converted material which is the desired product. Any improvement which results in either increasing the selectivity or the activity without lowering the other is economically attractive since the result is that the yield of the product (moles of desired product produced per mole of reactant) has been increased. An increase of only a few tenths of a percent in the selectivity can result in a substantial savings of starting materials while an increase in activity can substantially reduce capital expenditure and energy consumption.

The prior art catalysts used in the dehydrogenation of alkyl aromatics to alkenyl aromatics, for example, ethylbezzene to styrene as previously discussed, are widely known. Early dehydrogenation patents describe the use of cerium oxide as the major active ingredient. Thus, for example, U.S. Pat. No. 1,985,844 discloses the use of cerium oxide precipitated on broken pieces of clay to dehydrogenate ethylbenzene below atmospheric pressure. Another, U.S. Pat. No. 2,036,410, discloses the use of cerium oxide promoted with oxides of tungsten, uranium, and molybdenum.

Various catalysts, dehydrogenation conditions and other operating data are disclosed by Pitzer in U.S. Pat. No. 2,866,790 relating to the use of a catalyst composition including potassium carbonate, chromium oxide, and iron oxide. Other catalysts and procedures are also shown by Gutzeit, U.S. Pat. No. 2,408,140: Eggertsen, et al., U.S. Pat. No. 2,414,585; Hills, et al, U.S. Pat. No. 3,360,579; and Riesser, U.S. Pat. No. 4,098,723.

O'Hara, in U.S. Pat. No. 3,904,552, discloses the use of cerium and molybdenum in alkali promoted iron oxide dehydrogenation catalysts.

MacFarlane, in U.S. Pat. No. 3,223,743, teaches that it is very difficult to obtain a catalyst which has both high selectivity and high activity since as one increases, the other usually decreases. To overcome this he teaches the use of two layers of catalyst, the first layer with high selectivity (lower activity) and a second layer with high activity (lower selectivity). The first layer may contain 20–80% by weight iron and 0.5–5% by weight cerium oxide.

Riesser, in U.S. Pat. No. 4,144,197, discloses the use of vanadium to improve the selectivity of a potassium promoted dehydrogenation catalyst containing 20–95% by weight ferric oxide and 0.01–50% by weight cerous oxide. Data in the '197 patent is consistent with the teaching of MacFarlane with respect to vanadium addition since increasing amounts increase the selectivity at the sacrifice of activity. Also disclosing the use of cerium as a promoter in iron oxide based catalysts is U.S. Pat. No. 4,467,046.

A copending application of two of the inventors of the present invention discloses a catalyst formulation containing low concentrations of iron in combination with high concentrations of potassium and cerium. The referenced application, Ser. No. 69,464, filed July 1, 1987 is entitled "Dehydrogenation Catalyst".

Patents which show the use of copper as a stablizer for dehydrogenation catalysts include U.S. Pat. Nos. 2,395,875 and 2,395,876 which disclose catalysts containing a major amount of magnesium oxide, a minor amount of iron oxide together with an alkali or alkaline earth promoter and a copper oxide stablizer. A zinc oxide based catalyst containing a minor amount of iron oxide, promoted with potassium oxide and stabilized with copper oxide is disclosed in U.S. Pat. No. 2,418,888 while U.S. Pat. No. 2,418,889 discloses a similar beryllium oxide based catalyst. U.S. Pat. No. 2,426,829 which discloses an alkali promoted iron oxide dehydrogenation catalyst indicates that oxides of aluminum, zinc or copper may be added as a stabilizers.

Other patents teaching the use of copper oxide as a stabilizer for alkali-promoted iron oxide catalysts are U.S. Pat. Nos. 3,387,053; 3,448,058; 3,542,897; 4,064,187 and 4,134,858. Other catalysts in which copper is the primary or major component include those disclosed in U.S. Pat. Nos. 4,279,777; 4,334,116 and 4,590,324.

It has now been discovered that an alkali promoted iron/cerium dehydrogenation catalyst can be improved with respect to its activity, with little or no effect on selectivity, by the addition of a copper compound.

While copper has been employed as a stabilizer in some iron dehydrogenation catalysts, as above indicated, its combination with cerium in the presently disclosed catalyst compositions is novel and provides unexpected benefits.

SUMMARY OF THE INVENTION

A dehydrogenation catalyst having improved activity has been made by adding a copper compound to an alkali-promoted iron catalyst containing cerium. The copper provides an unexpected improvement in the activity of such catalysts.

DETAILED DESCRIPTION OF THE INVENTION

The catalyst compositions of the present invention contain, by weight, from about 5 to about 70% iron as $Fe_2O_3$, preferably from about 15 to about 60% from about 10 to about 60% potassium as $K_2CO_3$, preferably from about 20 to about 55%: from about 10 to about 60% cerium as $Ce_2O_3$ preferably from about 12 to about 30% and from about 0.1 to about 50% copper as CuO, preferably from about 1 to about 15% based on the total weight of the finished calcined catalyst.

Iron is generally added to the compositions of the invention as the oxide. While various forms of iron oxide can be employed in the compositions of the present invention, the preferred form is a mixture of red iron oxide ($Fe_2O_3$) and yellow iron oxide ($Fe_2O_3.H_2O$). When the mixture of oxides is employed, about 30% to about 70% of the total moles of iron oxide is added as yellow iron oxide. The amount preferred is about 40–60 molar percent of the yellow oxide and the most preferred is about 50 molar percent. Particularly suited are pigment grade red and yellow iron oxides.

The catalyst compositions of the present invention also contain as a catalyst promoter, an alkali metal compound, e.g. a potassium compound. The potassium promoter can be added to the catalyst in various forms. For example, it may be added as the oxide, or as other compounds which are convertible, at least in part, under calcination conditions, to the oxide. The hydroxides, carbonates, bicarbonates, and the like are suitable. The potassium compound is preferably present in the catalyst as potassium carbonate or as a mixture thereof with potassium oxide.

Cerium as used in the catalyst compositions of the present invention can be added to the catalyst in the form of cerium oxide or in the form of other cerium compounds which decompose upon calcination to form cerium oxide, as for example, cerium carbonate, cerium nitrate and cerium hydroxide.

Copper can be added to the catalyst formulations of the invention as its oxides, hydroxides, carbonates, acetates, nitrates or sulfates and the like.

Other known catalyst additives can be included in the catalysts of the invention, but are not essential. Thus, an optional component of the catalyst composition of the invention is a chromium compound which serves as a stabilizer for the active catalytic components. Chromium compounds have, in fact, typically been added to alkali-promoted iron oxide catalysts to extend their life. Chromium, as used in the compositions of this invention, can be added to the catalyst in the form of a chromium oxide or in the form of chromium compounds which decompose upon calcination to chromium oxides, as for example, chromium nitrates, hydroxides, acetates, and the like. If potassium chromates are used, such materials can, of course, also contribute to the requisite concentration of potassium present in the dehydrogenation catalyst compositions as hereinbefore discussed. Catalyst compositions of the invention optionally contain up to about 5% by weight, preferably (when employed) from about 0.5% to 3%, of a chromium compound, expressed as $Cr_2O_3$.

A second optional component, used to improve the selectivity of the catalyst, is molybdenum which can be added as its oxide or as a molybdate. The molybdenum component is present (when employed) in an amount up to about 2.5% by weight, preferably about 0.2 to about 1.5% molybdenum, calculated as $MoO_3$.

The physical strength, activity and selectivity of the catalyst compositions of the present invention can be improved by adding certain binding agents. Binding agents can include, for example, calcium aluminate or Portland cement. These cements can be added individually or in combination. The catalyst should contain from about 3% to about 20% by weight hydraulic cement, preferably from about 5% to about 15%. Calcium also can be added as its sulfate and/or its carbonate as a supplement to, or replacement for a part of, the binder component.

The density of the catalyst composition herein can likewise be modified by the addition of various filler substances, for example, combustible materials such as graphite and methyl cellulose. Such materials can be added to the compositions during preparation, but are burned out after the catalyst pellets have been formed during the calcining step. These porosity promoting aids can also facilitate extrusion of catalyst pellets. These fillers generally comprise up to about 10% by weight of the catalyst composition, preferably from about 2 to about 8 percent.

The catalyst compositions of the present invention generally are prepared by admixing the essential and desired optional components heretofore described and by drying and calcining the resulting mixture. Calcination temperatures can range from about 500° C. to about 800° C., preferably from about 550° C. to about 750° C. The catalyst compositions of the present invention can be prepared in various ways known to the art.

One method comprises ballmilling together a mixture of the desired compounds, adding a small amount of water, and extruding the composite to produce small pellets, which are then dried and calcined. Another method is mixing the components together with water, drying them to form a powder and tabletizing. Another procedure involves mixing the components together with an excess of water, partially drying, and then subsequently extruding, drying and calcining the resulting pellets.

The catalysts of the present invention are especially effective in promoting the dehydrogenation of ethylbenzene to produce styrene. Such a dehydrogenation reaction is usually carried out at reaction temperatures of from about 500° C. to about 700° C. However, higher or lower temperatures may be used as are known to the art. The use of subatmospheric, atmospheric, or superatmospheric pressures are suitable. However, since it is preferred to operate at as low a pressure as is feasible, atmospheric or subatmospheric pressure is preferred. The process of the invention preferably is carried out as a continuous operation. It is preferred to utilize a fixed bed which may consist of a single stage or a series of stages of the same catalyst in one or several reactors.

With the use of the catalyst of this invention, it is desirable to add steam to the hydrocarbon reactant feed to aid in the removal of carbonaceous residues from the catalyst. Steam to hydrocarbon weight ratios of from about 0.5:1 to about 5:1 are desirable depending on the compound being dehydrogenated. Best results are obtained with steam to hydrocarbon ratios above about 1:1.

The contact time of the reactant-containing gas with the catalyst is usually expressed in terms of liquid-hourly-space velocity (LHSV), which is defined as the volume of liquid hydrocarbon reactant per volume of catalyst per hour. The LHSV of the organic reactants, e.g. ethylbenzene, according to this invention may vary depending upon the reactant and is preferably adjusted within the range of from about 0.3 to 10 to effect the degree of conversion desired for the particular feed in question.

It should be noted that advantages resulting from increases in activity as indicated by a difference of a few degrees of temperature are extremely significant in a commercial process which may produce many hundreds of thousand pounds of product per day. The catalysts of the present invention and their use will be further described by the following illustrative examples which are representative of the invention.

5

Throughout the specification the examples of the invention are numbered numerically, while comparative examples are identified by letters, i.e. A,B,C, etc.

EXAMPLE 1

A catalyst formulation was made by blending 130 g red iron oxide ($Fe_2O_3$), 147.7 g yellow iron oxide ($Fe_2O_3.H_2O$), 79.4 g $Ce_2(CO_3)_3.5H_2O$, 450 g $K_2CO_3$, 69 g $CuCO_3.Cu(OH)_2$, 10 g $MoO_3$, 38 g $CaSO_4.2H_2O$ (gypsum), 27 g $CaCO_3$, 60 g calcium aluminate cement (LUMNITE*), 20 g amorphous graphite and 10 g methyl cellulose. About 116 mL of deionized water was added to the dry ingredients. The ingredients were thoroughly mixed, heated and dried to a consistency suitable for extrusion. The pellets (5/32", 0.397 cm., in diamter) were extruded and then calcined at a temperature of from 550° to 650° C. for a period of about 2½ hrs.
*LUMNITE is a trademark of the Lehigh Cement Company.

EXAMPLES 2 AND 3

Two more catalysts were prepared according to the procedure of Example 1, except that they contained different weight percentages of the components.

EXAMPLES A, B AND C (COMPARATIVE)

The same procedure employed in the above examples was used to make catalysts similar to those of Examples 1-3, except that they contained no copper.

The catalyst compositions of Examples 1-3 and A-C, expressed as shown, are given in Table I.

TABLE I

| | Components (weight percent) | | | | | | | |
|---|---|---|---|---|---|---|---|---|
| Ex. No. | $Fe_2O_3$ | $Ce_2O_3$ | $K_2CO_3$ | $MoO_3$ | CuO | LUMNITE | $CaSO_4$ | $CaCO_3$ |
| A | 29.3 | 5.6 | 50.7 | 1.1 | — | 6.8 | 3.4 | 3.0 |
| 1 | 27.8 | 5.3 | 48.0 | 1.1 | 5.3 | 6.4 | 3.2 | 2.9 |
| B | 39.7 | 13.2 | 33.1 | 1.1 | — | 6.6 | 3.3 | 3.0 |
| 2 | 37.7 | 12.5 | 31.3 | 1.0 | 5.2 | 6.3 | 3.1 | 2.8 |
| C | 14.6 | 23.6 | 48.2 | 1.1 | — | 6.4 | 3.2 | 2.9 |
| 3 | 11.5 | 23.0 | 47.0 | 1.0 | 5.2 | 6.3 | 3.1 | 2.8 |

CATALYST TEST PROCEDURE

Each of the above catalysts of the invention and those prepared for comparison was tested for activity and selectivity in the reaction for dehydrogenating ethylbenzene to styrene by placing 70 mL of the above catalyst pellets in a fixed bed reactor and passing a preheated mixture of steam and ethylbenzene at a weight ratio of 1.5:1 through the bed which was maintained at a temperature to give the desired conversion of ethylbenzene, this temperature being dependent upon the activity of the particular catalyst. The LHSV was 1.0 and the pressure was maintained at atmospheric. The temperature was adjusted to produce a 50% conversion of ethylbenzene, that temperature being an indication of the activity of the particular catalyst.

The results of the dehydrogenation reaction for Examples 1-3 and A-C are shown in Table II.

TABLE II

| Ex. No. | Temp. (°C.) at 50% conversion | Percent Selectivity |
|---|---|---|
| A | 597 | 96.4 |
| 1 | 590 | 96.4 |
| B | 595 | 95.5 |
| 2 | 587 | 96.1 |
| C | 589 | 96.3 |

TABLE II-continued

| Ex. No. | Temp. (°C.) at 50% conversion | Percent Selectivity |
|---|---|---|
| 3 | 577 | 96.6 |

EXAMPLES 4-6

Three additional catalysts were prepared according to the procedure of Example 1, except that they contained different amounts of copper. The catalyst of Example 4 was calcined at a temperature of 700° C. for one-half hour, the higher temperature requiring a shorter period of time for the calcination. The catalysts of Examples 5 and 6 were calcined at the same temperature and for the same period of time as were the catalysts of Examples 1-3.

EXAMPLES 7-9

These three examples were also prepared according to the procedure of Example 1, except that the source of copper employed was $Cu(NO_3)_2.2½H_2O$.

EXAMPLE D (Comparative)

For comparison, a catalyst was prepared without copper, but otherwise similar to that of Example 4. It was calcined at the same temperature and for the same period of time as were the catalysts of Examples 1-3.

EXAMPLE 10

The catalyst of this example was prepared according to the procedure of Example 1 except that the catalyst contained no molybdenum.

EXAMPLE E (Comparative)

The catalyst of this example was prepared in the manner of Example 10, except that it contained no copper, in order to compare with a similar catalyst which contained no molybdenum.

The compositions of all of the above catalysts of Examples 4-10 and Examples D and E, expressed as shown, are given in Table III.

TABLE III

| Ex. No. | Components (weight percent) | | | | | | |
|---|---|---|---|---|---|---|---|
| | $Fe_2O_3$ | $Ce_2O_3$ | $K_2CO_3$ | $MoO_3$ | CuO | LUMNITE | $CaSO_4$ |
| 4 | 24.2 | 12.1 | 45.5 | 1.0 | 2.0 | 12.1 | 3.0 |
| 5 | 21.2 | 12.1 | 45.5 | 1.0 | 5.0 | 12.1 | 3.0 |
| 6 | 20.2 | 11.5 | 43.3 | 1.0 | 9.6 | 11.5 | 2.9 |
| 7 | 25.3 | 12.1 | 45.5 | 1.0 | 1.0 | 12.1 | 3.0 |
| 8 | 24.2 | 12.1 | 45.5 | 1.0 | 2.0 | 12.1 | 3.0 |
| 9 | 21.2 | 12.1 | 45.5 | 1.0 | 5.0 | 12.1 | 3.0 |
| D | 26.3 | 12.1 | 45.5 | 1.0 | — | 12.1 | 3.0 |
| 10 | 21.4 | 12.3 | 45.9 | — | 5.1 | 12.2 | 1.1 |

TABLE III-continued

| Ex. No. | Components (weight percent) | | | | | | |
|---|---|---|---|---|---|---|---|
| | Fe$_2$O$_3$ | Ce$_2$O$_3$ | K$_2$CO$_3$ | MoO$_3$ | CuO | LUM-NITE | CaSO$_4$ |
| E | 27.6 | 10.5 | 47.9 | — | — | 12.8 | 3.1 |

The results of testing the catalyst compositions shown in Table III in the dehydrogenation reaction described above under "Catalyst Test Procedure" are shown in Table IV.

TABLE IV

| Ex. No. | Temp. (°C.) at 50% conversion | Percent Selectivity |
|---|---|---|
| 4 | 588 | 96.8 |
| 5 | 585 | 96.6 |
| 6 | 587 | 96.3 |
| 7 | 591 | 96.2 |
| 8 | 587 | 96.3 |
| 9 | 585 | 96.9 |
| D | 592 | 96.6 |
| 10 | 595* | 95.2 |
| E | 605* | 95.8 |

*Examples 10 & E were run at 56% conversion.

We claim:

1. A dehydrogenation catalyst composition which comprises from about 5 to about 70% iron as Fe$_2$O$_3$, from about 10 to about 60% potassium as K$_2$CO$_3$, from about 2 to about 60% cerium as Ce$_2$O$_3$ and from about 0.1 to about 50% copper as CuO.

2. The composition of claim 1 wherein the amounts of iron, potassium, cerium and copper are from about 15 to about 60%, about 20 to about 55%, about 12 to about 30% and about 1 to about 15%, respectively.

3. The composition of claim 1 which contains a binder.

4. The composition of claim 3 wherein at least a portion of the binder is a hydraulic cement.

5. The composition of claim 4 wherein the binder is present in an amount of from about 3 to about 20 percent by weight of the total composition.

6. The composition of claim 2 which contains a binder.

7. The composition of claim 6 wherein at least a portion of the binder is a hydraulic cement.

8. The composition of claim 7 wherein the binder is present in an amount of from about 3 to about 15 percent by weight of the total composition.

9. The composition of claim 4 wherein the hydraulic cement is Portland cement.

10. The composition of claim 4 wherein the hydraulic cement is a calcium aluminate cement.

11. The composition of claim 7 wherein the hydraulic cement is Portland cement.

12. The composition of claim 7 wherein the hydraulic cement is a calcium aluminate cement.

13. The composition of claim 9 wherein a portion of the binder is calcium sulfate, calcium carbonate or mixtures thereof.

14. The composition of claim 10 wherein a portion of the binder is calcium sulfate, calcium carbonate or mixtures thereof.

15. The composition of claim 11 wherein a portion of the binder is calcium sulfate, calcium carbonate or mixtures thereof.

16. The composition of claim 12 wherein a portion of the binder is calcium sulfate, calcium carbonate or mixtures thereof.

17. The composition of claim 1 wherein the catalyst contains chromium or molybdenum promoters or a mixture thereof.

18. The composition of claim 17 wherein chromium is present in an amount of up to about 5 percent, calculated as Cr$_2$O$_3$.

19. The composition of claim 17 wherein molybdenum is present in an amount of up to about 2.5 percent, calculated as MoO$_3$.

20. The composition of claim 18 wherein a chromium promoter is present in an amount of about 0.5 to about 3 percent by weight, as Cr$_2$O$_3$.

21. The composition of Claim 19 wherein a molybdenum promoter is present in an amount of from about 0.2 to about 1.5 percent by weight, as MoO$_3$.

22. In a process for dehydrogenating an alkylaromatic compound to make an alkenyl aromatic compound in which the alkylaromatic compound is heated together with steam in the presence of an alkali-promoted iron catalyst containing cerium, the improvement which comprises employing said catalyst which additionally contains copper as a promoter.

23. The process of claim 22 wherein the catalyst comprises from about 5 to about 70% iron as Fe$_2$O$_3$, from about 10 to about 60% potassium as K$_2$CO$_3$, from about 2 to about 60% cerium as Ce$_2$O$_3$ and from about 0.1 to about 50% copper as CuO, all by weight in the finished catalyst.

24. The process of claim 23 wherein the iron, potassium, cerium and copper are present in amounts of from about 5 to about 60%, about 20 to about 55% about 12 to about 30% and about 1 to about 15%, respectively.

25. The process of claim 23 in which the catalyst composition contains a binder.

26. The process of claim 25 wherein at least a portion of the binder is a hydraulic cement.

27. The process of claim 26 in which the binder is present in an amount of from about 3 to about 20 percent by weight of the total composition.

28. The process of claim 24 wherein the composition contains a binder.

29. The process of claim 28 wherein at least a portion of the binder is a hydraulic cement 30. The process of claim 29 wherein the binder is present in an amount of from about 3 to about 15 percent by weight of the total composition.

31. The process of claim 26 wherein the hydraulic cement is Portland cement.

32. The process of claim 26 wherein the hydraulic cement is a calcium aluminate cement.

33. The process of claim 29 wherein the hydraulic cement is Portland cement.

34. The process of claim 29 wherein the hydraulic cement is a calcium aluminate cement.

35. The process of claim 31 wherein a portion of the binder is calcium sulfate, calcium carbonate or mixtures thereof.

36. The process of claim 32 wherein a portion of the binder is calcium sulfate, calcium carbonate or mixtures thereof.

37. The process of claim 33 wherein a portion of the binder is calcium sulfate, calcium carbonate or mixtures thereof.

38. The process of claim 34 wherein a portion of the binder is calcium sulfate, calcium carbonate or mixtures thereof.

39. The process of claim 23 wherein the catalyst contains chromium or molybdenum promoters or a mixture thereof.

40. The process of claim 25 wherein the catalyst contains chromium or molybdenum promoters or a mixture thereof.

41. The process of claim 40 wherein molybdenum is present in an amount of up to about 2.5 percent, calculated as $MoO_3$.

42. The process of claim 41 wherein molybdenum is present in an amount of from about 0.2 to about 1.5 percent, calculated as $MoO_3$.

* * * * *